United States Patent
Ogawa et al.

(10) Patent No.: US 9,782,332 B2
(45) Date of Patent: *Oct. 10, 2017

(54) HAIR BLEACHING OR HAIR DYE COSMETICS

(71) Applicant: KAO CORPORATION, Chuo-ku (JP)

(72) Inventors: Toshio Ogawa, Bunkyo-ku (JP); Yujiro Nakano, Kawasaki (JP); Shoichiro Kamitakahara, Koto-ku (JP); Yasuyuki Murase, Adachi-ku (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/031,873

(22) PCT Filed: Oct. 24, 2014

(86) PCT No.: PCT/JP2014/078287
§ 371 (c)(1),
(2) Date: Apr. 25, 2016

(87) PCT Pub. No.: WO2015/060416
PCT Pub. Date: Apr. 30, 2015

(65) Prior Publication Data
US 2016/0262994 A1  Sep. 15, 2016

(30) Foreign Application Priority Data

Oct. 25, 2013 (JP) ................... 2013-222512
Oct. 25, 2013 (JP) ................... 2013-222515
Oct. 25, 2013 (JP) ................... 2013-222516

(51) Int. Cl.
| | |
|---|---|
| *A61K 8/22* | (2006.01) |
| *A61K 8/41* | (2006.01) |
| *A61K 8/46* | (2006.01) |
| *A61Q 5/08* | (2006.01) |
| *A61Q 5/10* | (2006.01) |
| *A61K 8/81* | (2006.01) |
| *A61K 8/04* | (2006.01) |

(52) U.S. Cl.
CPC ............... *A61K 8/22* (2013.01); *A61K 8/046* (2013.01); *A61K 8/41* (2013.01); *A61K 8/415* (2013.01); *A61K 8/416* (2013.01); *A61K 8/463* (2013.01); *A61K 8/817* (2013.01); *A61Q 5/08* (2013.01); *A61Q 5/10* (2013.01); *A61K 2800/87* (2013.01)

(58) Field of Classification Search
CPC ........ A61K 8/463; A61K 8/817; A61K 8/416; A61K 8/415; A61K 8/22; A61K 8/41; A61K 8/046; A61Q 5/08; A61Q 5/10
See application file for complete search history.

(56) References Cited

U.S. PATENT DOCUMENTS

| | | | | |
|---|---|---|---|---|
| 8,025,703 | B2 * | 9/2011 | Ogawa ................... | A61K 8/046 8/405 |
| 8,153,108 | B2 * | 4/2012 | Fujinuma ............... | A61K 8/046 424/62 |
| 8,158,112 | B2 * | 4/2012 | Fujinuma ............... | A61K 8/046 424/62 |
| 8,277,784 | B2 * | 10/2012 | Fujinuma ............... | A61K 8/046 424/62 |
| 8,349,022 | B2 * | 1/2013 | Iijima ................... | A61K 8/046 8/405 |
| 2004/0213752 | A1 | 10/2004 | Fujinuma et al. | |
| 2010/0257677 | A1 | 10/2010 | Miyabe et al. | |
| 2011/0277782 | A1 * | 11/2011 | Iijima ................... | A61K 8/046 132/208 |
| 2013/0298934 | A1 | 11/2013 | Goget et al. | |

FOREIGN PATENT DOCUMENTS

| | | |
|---|---|---|
| EP | 2 204 160 A1 | 7/2010 |
| EP | 2 283 803 A1 | 2/2011 |
| JP | 2002-284655 A | 10/2002 |
| JP | 2004-75644 A | 3/2004 |
| JP | 2004-339216 A | 12/2004 |
| JP | 2008-19185 A | 1/2008 |
| JP | 2009-120601 A | 6/2009 |
| JP | 2010/235581 A | 10/2010 |
| WO | 2010/103795 A1 | 9/2010 |
| WO | 2010/103796 A1 | 9/2010 |
| WO | 2012/059410 A1 | 5/2012 |
| WO | WO 2012/059410 A1 * | 5/2012 |
| WO | WO 2012/117858 A1 | 9/2012 |

OTHER PUBLICATIONS

International Search Report issued Jan. 27, 2015, in PCT/JP2014/078287 Filed Oct. 24, 2014.
Extended European Search Report issued Mar. 20, 2017 in Patent Application No. 14856515.3.

* cited by examiner

*Primary Examiner* — Blessing M Fubara
(74) *Attorney, Agent, or Firm* — Oblon, McClelland, Maier & Neustadt, L.L.P.

(57) ABSTRACT

Provided is a cosmetic product for hair bleaching or hair dyeing comprising a first agent comprising an alkali agent, a second agent comprising hydrogen peroxide, and a nonaerosol foamer container for discharging a mixed solution thereof in the form of foam, the mixed solution comprising the following components (A) to (C), (A) a anionic surfactant comprising sulfuric acid group, (B) anionic surfactant comprising carboxy group, and (C) a polymer comprising a diallyl quaternary ammonium salt as a constitutional unit and having a charge density of 5.5 meq/g or more and 8.0 meq/g or less.

16 Claims, No Drawings

HAIR BLEACHING OR HAIR DYE COSMETICS

FIELD OF THE INVENTION

The present invention relates to a cosmetic product for hair bleaching or hair dyeing.

BACKGROUND OF THE INVENTION

Hair bleaches and hair dyes having been commonly used for a long time, which are in the liquid form or cream form are difficult to apply these products to hair evenly. The application particularly to the roots of hairs and the back of the head requires skills such as blocking or using two-mirror technique, consequently time consuming.

Under the circumstances, simplified bleaching or dyeing operation by discharging the agent in the form of foam is proposed, and for example two-agent aerosol type products and one-agent nonaerosol type products are known. However, two-agent aerosol type products pose problems in that uneven bleaching and uneven dyeing are likely to be caused, a pressure resistant metal container, and the like, are oxidized and corroded by hydrogen peroxide, and an internal pressure of a pressure resistant container is excessively increased by the decomposition of hydrogen peroxide, whereas one-agent nonaerosol type products have drawbacks of providing an ineffective result from a single treatment, consequently necessitating to wait for a long time after application or repeat treatments, hence cumbersome.

As a counter measurement, a product for discharging a two-agent hair bleach or a two-agent hair dye from a nonaerosol type foamer container has been proposed (see Patent Document 1). Such a product, by discharging a mixed solution of the first agent and the second agent in the form of foam from a foamer container, enables an even application to hair, prevents uneven colors when finished because the foam sufficiently stays, and is particularly useful for solving color level differences between the newly grown portion and the already dyed portion.
(Patent Document 1) JP-A-2004-339216

SUMMARY OF THE INVENTION

The present invention provides a cosmetic product for hair bleaching or hair dyeing comprising a first agent comprising an alkali agent, a second agent comprising hydrogen peroxide, and a nonaerosol foamer container for discharging a mixed solution of the first agent and the second agent in the form of foam, the mixed solution comprising the following components (A) to (C).

(A) an anionic surfactant comprising sulfuric acid group,
(B) an anionic surfactant comprising carboxy group, and
(C) a polymer comprising a diallyl quaternary ammonium salt as a constitutional unit and having a charge density of 5.5 meq/g or more and 8.0 meq/g or less.

The present invention further provides a method for bleaching or dyeing hair by using the above cosmetic product for hair bleaching or hair dyeing, discharging the mixed solution of the first agent and the second agent from a nonaerosol foamer container in the form of foam, and applying the foam to hair with a hand.

DETAILED DESCRIPTION OF THE INVENTION

The nonaerosol type two-agent cosmetic product for hair bleaching or hair dyeing described above can achieve an even dye by a simple operation but when applied to hair with an out bath treatment or a conditioner adhered thereto, the foam is likely to disappear and dripping may easily be caused while applying the foam hair or retaining the foam on hair, failing to dye hair satisfactorily without unevenness in such a case, hence problematic.

The present invention relates to a nonaerosol type cosmetic product for hair bleaching or hair dyeing, which has good foaming performance (foaming and foam retention) even for hair with an out bath treatment or a conditioner adhered thereto and good applicability for bleaching or dyeing without causing uneven colors while maintaining the benefits of the nonaerosol type two-agent cosmetic product for hair bleaching or hair dyeing described in Patent Document 1.

The present inventors found that the above problems can be solved when a specific anionic surfactant and a specific cationic polymer are added to the mixed solution of the first agent and the second agent in the nonaerosol type cosmetic product for hair bleaching or hair dyeing.

The cosmetic product for hair bleaching or hair dyeing of the present invention can be used as a two-agent cosmetic product, which is used by mixing a first agent and a second agent, or as a three-agent cosmetic product, which is used by further mixing a third agent such as persulfates in the form of granule in addition to the first agent and the second agent. In the present invention, the mixed solution means a mixed solution of the first agent and the second agent in the case of the two-agent cosmetic product and a mixed solution of the first agent, the second agent, and the third agent in the case of the three-agent cosmetic product.

[Alkali Agent]

The first agent contains an alkali agent. Examples of the alkali agent include ammonia and salts thereof (e.g., ammonium hydrogencarbonate); alkanolamine and salts thereof such as monoethanolamine, isopropanolamine, 2-amino-2-methylpropanol, and 2-aminobutanol; alkanediamine and salts thereof such as 1,3-propanediamine; and carbonates such as guanidine carbonate, sodium carbonate, potassium carbonate, sodium bicarbonate, and potassium hydrogencarbonate. Two or more of these alkali agents may be used in combination. A content of the alkali agent in the mixed solution is, from the viewpoint of sufficient hair dyeing effects, preferably 0.05 mass % or more, more preferably 0.1 mass % or more, and further preferably 0.2 mass % or more, and is, from the viewpoint of reducing hair damages and scalp irritation, preferably 15 mass % or less, more preferably 10 mass % or less, and further preferably 5 mass % or less.

[Hydrogen Peroxide]

The second agent contains hydrogen peroxide. A content of the hydrogen peroxide in the second agent is preferably 1 mass % or more, and more preferably 3 mass % or more, and is preferably 9 mass % less, and more preferably 6 mass % or less. A content of the hydrogen peroxide in the mixed solution is preferably 1 mass % or more, and more preferably 2 mass % or more, and is preferably 6 mass % or less, and more preferably 5 mass % or less. pH of the second agent is, from the viewpoint of preventing the hydrogen peroxide decomposition, preferably 2 or more, and more preferably 2.5 or more, and is preferably 6 or less, and more preferably 4 or less.

[Component (A): Anionic Surfactant Comprising Sulfuric Acid Group]

The cosmetic product for hair bleaching or hair dyeing of the present invention contains a anionic surfactant comprising sulfuric acid group in the mixed solution. As the anionic surfactant comprising sulfuric acid group, a anionic surfactant comprising sulfuric acid group represented by the following formula (1) can be used.

$$R—O—(CH_2CH_2O)_n—[CH_2CH(CH_3)O]_m—SO_3M \qquad (1)$$

wherein R represents a hydrocarbon group having 8 to 25 carbon atoms, n represents an average number of moles added of 0 to 50, m represents an average number of moles added of 0 to 50, and M represents an alkali metal atom or $NH_4$.

R in the formula (1) has preferably 8 to 24 carbon atoms, more preferably 10 to 22 carbon atoms, and further preferably 10 to 18 carbon atoms. Further, R is preferably a linear chain or branched chain alkyl group or alkenyl group, and more preferably a linear chain alkyl group.

n in the formula (1) is, from the viewpoint of foaming properties for hair subjected to a treatment, preferably 0.5 or more, and more preferably 1 or more, and is preferably 45 or less, more preferably 30 or less, further preferably 15 or less, and further preferably 10 or less.

m in the formula (1) is, from the viewpoint of foaming properties for hair subjected to a treatment, preferably 30 or less, more preferably 10 or less, further preferably 5 or less, and further more preferably 0.

M in the formula (1), a salt-forming cationic group, is an alkali metal atom or $NH_4$. Examples of the alkali metal atom include sodium, potassium, and lithium atom, with sodium and potassium being more preferable, and sodium being further preferable.

The addition form of the $(CH_2CH_2O)$ and $[CH_2CH(CH_3)O]$ in the component (A) may be block or random.

The component (A) may be added to any of the first agent, the second agent or the third agent when the cosmetic product for hair bleaching or hair dyeing is the two-agent type or three-agent type.

A content of the component (A) in the mixed solution is, from the viewpoints of foaming and foam retention on hair subjected to a treatment, preferably 0.01 mass % or more, more preferably 0.1 mass % or more, further preferably 0.5 mass % or more, and further preferably 0.7 mass % or more, and is preferably 20 mass % or less, more preferably 10 mass % or less, further preferably 5 mass % or less, further preferably 3 mass % or less, further preferably 2 mass % or less, and further preferably 1.5 mass % or less.

[Component (B): Anionic Surfactant Comprising Carboxy Group]

The cosmetic product for hair bleaching or hair dyeing of the present invention contains a anionic surfactant comprising carboxy group in the mixed solution from the viewpoints of foaming and foam retention on hair subjected to a treatment. Examples of the anionic surfactant comprising carboxy group include N-acylamino acid salts, N-acyl-N-alkylamino acid salts, amide type N-acylamino acid salts, ether carboxylates, fatty acid salts, and salts of alkyl succinic acid and alkenyl succinic acid.

Examples of the amino acid residue of N-acylamino acid salt used herein include glutamic acid and aspartic acid, and examples of the amino acid residue of N-acyl-N-alkylamino acid salt include glutamic acid, glycine, and β-alanine. Examples of the alkyl group of N-acyl-N-alkylamino acid salt include methyl groups, ethyl groups, propyl groups, and isopropyl groups. Examples of the acyl group include lauroyl groups, myristoyl groups, and palmitoyl groups, and examples of the salt thereof include salts of sodium, potassium, lithium, ethanolamine, diethanolamine, and triethanolamine (hereinafter abbreviated to as TEA) and the like. As preferable specific examples of these include N-lauroyl glutamate, N-myristoyl glutamate, and N-cocoyl glutamate for the N-acylamino acid, and N-lauroyl-N-isopropylglycine, N-lauroylsarcosine, N-myristoylsarcosine, N-palmitoylsarcosine, and N-lauroyl-N-methyl-β-alanine for the N-acyl-N-alkylamino acid.

Examples of the amide type N-acylamino acid salt include amide type N-acylamino acid salts represented by the following formula (2).

$$R^1CONH(CH_2)_pCOOM^1 \qquad (2)$$

wherein $R^1CO$ represents an acyl group having 10 to 22 carbon atoms, p represents a number of 1 or 2, $M^1$ represents sodium, potassium or alkanolammonium when p is 1 and represents potassium or alkanolammonium when p is 2.

In the above amide type N-acylamino acid salt, the acyl group represented by $R^1CO$ in the above formula (2) is desirably a linear chain, and specifically preferably a caprinoyl group, a lauroyl group, or a myristoyl group.

Examples of the ether carboxylate include polyglyceryl alkyl ether acetates or ether acetates represented by the following formula (3).

$$R^2—Z—(CH_2CH_2O)_q—CH_2COOM^2 \qquad (3)$$

wherein $R^2$ represents a linear chain or branched chain alkyl group or alkenyl group having 7 to 19 carbon atoms, Z represents —O— or —CONH—, $M^2$ represents a hydrogen atom, an alkali metal atom, triethanolamine or ammonium, and q represents a number of 1 to 20.

In the above ether acetates, those wherein $R^2$ has 11 to 15 carbon atoms are preferable. Further, q is preferably 3 to 15, and particularly preferably 6 to 12. Specific examples include polyoxyethylene (10) lauryl ether acetate (in the formula (3), $R^2=C_{12}H_{25}$, Z=—O—, q=10), polyoxyethylene (8) myristyl ether acetate (in the formula (3), $R^2=C_{14}H_{29}$, Z=—O—, q=8), lauric acid amide polyoxyethylene (6) ether acetate (in the formula (3), $R^2=C_{11}H_{23}$, Z=—CONH—, q=6), and lauric acid amide polyoxyethylene (10) ether acetate (in the formula (3), $R^2=C_{11}H_{23}$, Z=—CONH—, q=10). A degree of neutralization thereof is preferably 60 to 120%, and $M^2$ is preferably an alkali metal atom, and particularly preferably potassium.

Examples of the fatty acid salt include base salts of fatty acids having 8 to 22 carbon atoms. Specific examples can include base salts of, in addition to single fatty acids such as lauric acid, myristic acid, palmitic acid, isostearic acid, and oleic acid, mixed fatty acids such as coconut oil fatty acid and tallow acid. Examples of the salt used herein include inorganic basic salts such as sodium and potassium, alkanolamine salts such as ammonium salts, ethanolamine salts, diethanolamine salts, triethanolamine salts, 2-amino-2-methyl propanol, 2-amino-2-methyl propanediol, and basic amino acids such as lysine and arginine.

Examples of the alkyl group or the alkenyl group in salts of alkylsuccinic acid or alkenylsuccinic acid include hydrocarbon groups having 8 to 22 carbon atoms, specifically lauryl, myristyl, cetyl, stearyl, and oleyl, and each salt thereof such as sodium, potassium, lithium, ethanolamine, diethanolamine, and triethanolamine are included.

Two or more of these anionic surfactant comprising carboxy groups may be used in combination and contained in either one of the first agent or the second agent or in both of the parts. A content of the component (B) in the mixed solution is, for forming the foam which is easily applicable to and blendable with hair, preferably 0.01 mass % or more, more preferably 0.1 mass % or more, further preferably 0.5 mass % or more, and further preferably 0.7 mass % or more, and is preferably 20 mass % or less, more preferably 10 mass % or less, further preferably 7 mass % or less, further preferably 5 mass % or less, further preferably 3 mass % or less, and further preferably 2 mass % or less.

A content of the components (A) and (B) in total in the mixed solution of the cosmetic product for hair bleaching or hair dyeing of the present invention is, from the viewpoints of foaming and foam retention on hair subjected to a treatment and a feel of hair, preferably 0.02 mass % or more, more preferably 0.2 mass % or more, further preferably 0.5 mass % or more, and further preferably 1 mass % or more, and is preferably 20 mass % or less, more preferably 10 mass % or less, further preferably 7 mass % or less, further preferably 5 mass % or less, further preferably 3 mass % or less, and further preferably 2.5 mass % or less.

[Component (C): Polymer Comprising a Diallyl Quaternary Ammonium Salt as a Constitutional Unit]

The cosmetic product for hair bleaching or hair dyeing of the present invention contains, in the mixed solution, a polymer comprising a diallyl quaternary ammonium salt as a constitutional unit and having a charge density of 5.5 meq/g or more and 8.0 meq/g or less. The charge density used herein in the present invention refers to the number of moles of a cationic group per g of the polymer×1,000 (meq/g).

A charge density of the component (C) is, from the viewpoints of foaming and foam retention on hair subjected to a treatment and a feel of hair, preferably 5.7 meq/g or more, more preferably 5.9 meq/g or more, and further preferably 6.1 meq/g or more, and is, from the viewpoint of stability in the part, preferably 6.5 meq/g or less.

The polymer of the component(C) is a polymer having the skeleton represented by the following formula (4) or (5).

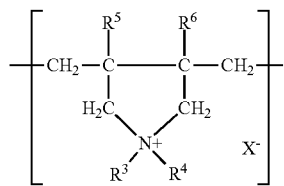

(4)

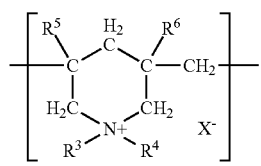

(5)

wherein $R^3$ and $R^4$ may be the same or different and represent a hydrogen atom, an alkyl group having 1 to 18 carbon atoms, an aryl group (a phenyl group, and the like), a hydroxyalkyl group, an amidoalkyl group, a cyanoalkyl group, an alkoxyalkyl group or a carboalkoxyalkyl group, $R^5$ and $R^6$ may be the same or different and represent a hydrogen atom, an alkyl group having 1 to 3 carbon atoms, or a phenyl group, $X^-$ represents an anion (chloride ion, bromide ion, iodide ion, sulfate anion, sulfonate anion, methyl sulfate anion, phosphate anion, nitrate amino or the like).

The polymer of the component (C) contains, from the viewpoints of foaming and foam retention on hair subjected to a treatment and a feel of hair, preferably 85 to 100 mol, more preferably 90 to 100 mol %, and further preferably 95 to 100 mol %, of the constitutional unit represented by the formula (4) or (5) in a single molecule.

The polymer to be the component (C) is preferably a homopolymer of diallyl quaternary ammonium salts and a copolymer of a diallyl quaternary ammonium salt and acrylic acid.

Preferable examples of the copolymer of a diallyl quaternary ammonium salt and acrylic acid include those represented by the following formula (4a) or (5a).

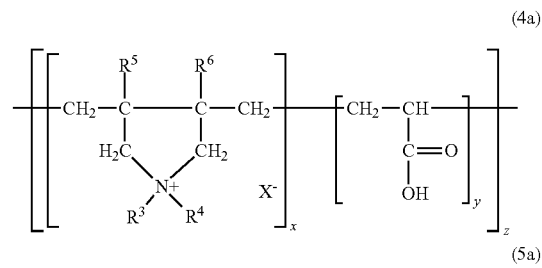

(4a)

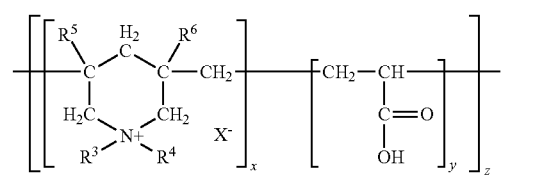

(5a)

In each of the formulae, $R^3$, $R^4$, $R^5$, $R^6$ and $X^-$ are defined as above, x and y each represent an integer of 1 to 100, and z represents an integer of 150 to 8,000.

A ratio of x to y (x:y) is, from the viewpoints of foaming properties on hair subjected to a treatment and a feel of hair, preferably 85:15 to 99:1, more preferably 90:10 to 99:1, and further preferably 95:5 to 99:1.

The addition form of x and y may be block or random.

A weight average molecular weight of the component (C) is, from the viewpoint of foam stability, preferably 10,000 or more, more preferably 50,000 or more, and further preferably 100,000 or more, and is, from the viewpoint of foam discharging performance, preferably 3,000,000 or less, more preferably 1,000,000 or less, and further preferably 200,000 or less.

The weight average molecular weight used herein can be measured by, for example, gel permeation chromatography (GPC) under the following conditions.

Mobile phase: 50 mM LiBr, 1 mass % $CH_3COOH$/ethanol:water =3:7

Column: TSK gel α-M (two series)

Standard substance: Polyethylene glycol

Specific examples of the component (C) include Merquat 100 (product of Lubrizol Corporation, a homopolymer of diallyl quaternary ammonium salts) and Merquat 295 (product of Lubrizol Corporation, a copolymer of a diallyl quaternary ammonium salt and acrylic acid).

The component (C) may be added to any of the first agent, the second agent or the third agent of the cosmetic product for hair bleaching or hair dyeing of the present invention.

A content of the component (C) in the mixed solution is, from the viewpoint of lasting effects, preferably 0.01 mass % or more, more preferably 0.1 mass % or more, further preferably 0.3 mass % or more, and is preferably 20 mass % or less, more preferably 10 mass % or less, further preferably 5 mass % or less, further preferably 3 mass % or less, further preferably 1.5 mass % or less.

A mass ratio of the components (A) and (B) in total to the component (C), [(A)+(B)]/(C), in the mixed solution of the cosmetic Product for hair bleaching or hair dyeing of the present invention is, from the viewpoints of foaming and foam retention on hair subjected to a treatment and a feel of hair, preferably 0.1 or more, more preferably 0.5 or more, further preferably 1 or more, further preferably 1.5 or more, further preferably 2 or more, and further preferably 3 or more, and is preferably 15 or less, more preferably 12 or less, further preferably 10 or less, and further preferably 5 or less.

[Component (D): Cationic Surfactant]

The cosmetic product for hair bleaching or hair dyeing of the present invention can contain, from the viewpoint of foam lasting effects, a cationic surfactant as a component (D) in either one of the first agent or the second agent or in both of the parts. Examples of the cationic surfactant as the component (D) including those represented by the following formula (6) can be used.

(6)

wherein $R^7$, $R^8$, $R^9$ and $R^{10}$ each independently represent a hydrocarbon group optionally having a substituent, one or two of $R^7$, $R^8$, $R^9$ and $R^{10}$ have 8 to 36 carbon atoms, and the remainder has 1 to 7 carbon atoms, and $X^-$ represents an anion.

Examples of the hydrocarbon group used herein include linear chain or branched chain alkyl groups, linear chain or branched chain alkenyl groups, aryl groups, and aralkyl groups, and examples of the substituent include hydroxy groups, alkoxy groups, aryloxy groups, epoxy groups, amino groups, mono- or dialkylamino groups, trialkyl ammonium groups, fatty acid amido groups, and fatty acid ester groups.

One or two (preferably one) of $R^7$, $R^8$, $R^9$ and $R^{10}$ is preferably a linear chain or branched chain alkyl group having 8 to 30 carbon atoms, further preferably 10 to 24 carbon atoms, and further preferably 12 to 18 carbon atoms, and the remainder is preferably an alkyl group having 1 to 3 carbon atoms, further preferably 1 or 2 carbon atoms, and further preferably 1 carbon atom.

Example of the anion include chloride ions, bromide ions, iodide ions, methyl sulfate ions, ethyl sulfate ions, acetate ions, phosphate ions, sulfate ions, lactate ions, and saccharin ions, of which chloride ions and bromide ions are preferable from the viewpoint of easy availability.

Specific examples of the component (D) include cetyltrimethylammonium chloride (cetrimonium chloride), stearyltrimethylammonium chloride (steartrimonium chloride), isostearyltrimethylammonium chloride (isosteartrimonium chloride), lauryltrimethylammonium chloride (laurtrimonium chloride), behenyltrimethyl ammonium chloride (behentrimonium chloride), cocoyltrimethylammonium chloride (cocotrimonium chloride), cetyltrimethylammonium bromide (cetrimonium bromide), stearyltrimethylammonium bromide (steartrimonium bromide), lauryltrimethylammonium bromide (laurtrimonium bromide), isostearyllauryldimethylammonium chloride (isostearyllauryldimonium chloride), dicetyldimethylammonium chloride (dicetyldimonium chloride), distearyldimethylammonium chloride (distearyldimonium chloride), and dicocoyldimethylammonium chloride (dicocodimonium chloride).

The component (D) is preferably monoalkyltrimethylammonium chloride and monoalkyltrimethylammonium bromide, of which stearyltrimethylammonium chloride (steartrimonium chloride), cetyltrimethylammonium chloride (cetrimonium chloride), and lauryltrimethylammonium chloride (laurtrimonium chloride) being more preferable.

Two or more of the component (D) may be used in combination and contained in either one of the first agent or the second agent or in both of the parts. A content of the component (D) in the mixed solution is, from the viewpoints of foaming and applicability, preferably 0.05 mass % or more, more preferably 0.2 mass % or more, and further preferably 0.4 mass % or more, and is preferably 5 mass % or less, more preferably 4 mass % or less, and further preferably 3 mass % or less.

[Component (E): Higher Alcohol]

The cosmetic product for hair bleaching or hair dyeing of the present invention can contain, from the viewpoint of foam stability, a higher alcohol as a component (E) in either one of the first agent or the second agent or in both of the parts. The component (E) represented by the following formula (7) may be used.

(7)

wherein $R^{11}$ represents a linear chain or branched chain hydrocarbon group having 12 to 24 carbon atoms.

$R^{11}$ in the formula (7) has, from the viewpoint of foam stability, preferably 10 to 24 carbon atoms, more preferably 12 to 22 carbon atoms, and further preferably 14 to 22 carbon atoms. $R^{11}$ is preferably a linear chain or branched chain alkyl group alkenyl group, and more preferably a linear chain alkyl group.

Specific examples of the higher alcohol include myristyl alcohol, cetanol, stearyl alcohol, arachyl alcohol, behenyl alcohol, and oleyl alcohol.

Two or more of the component (E) may be used in combination and contained in either one of the first agent or the second agent or in both of the parts. A content of the component (E) in the mixed solution is, from the viewpoint of foam discharging performance, preferably 0.05 mass % or more, more preferably 0.2 mass % or more, and further preferably 0.4 mass % or more, and is preferably 5 mass % or less, more preferably 4 mass % or less, and further preferably 3 mass % or less.

[Nonionic Surfactant]

The cosmetic product for hair bleaching or hair dyeing of the present invention may further contain a nonionic surfactant in either one of the first agent or the second agent or in both of the parts. Examples of the nonionic surfactant include polyoxyalkylene alkyl ether, alkyl alkanolamide, polyoxyalkylene alkylamine, alkyl polyglucoside, and alkyl glyceryl ether.

Polyoxyalkylene alkyl ether represented by the following formula (8) may be used.

(8)

wherein $R^{12}$ represents a linear chain or branched chain saturated or unsaturated hydrocarbon group having 8 to 22 carbon atoms, A represents an alkylene group having 2 to 4 carbon atoms, and r represents a number of 1 to 100 as an average value.

The number of carbon atoms of $R^{12}$ is, from the viewpoints of foaming of the hair dye and the solubility of the dye contained in the hair dye, preferably 10 to 22, further preferably 12 to 20, and further preferably 12 to 18.

A is preferably an ethylene group or a propylene group, with an ethylene group being more preferable.

r is preferably 1 to 40, further preferably 2 to 30, and further preferably 4 to 23.

Specific examples of the polyoxyalkylene alkyl ether include polyoxyethylene lauryl ether, polyoxyethylene cetyl ether, polyoxyethylene stearyl ether, and polyoxyethylene oleyl ether.

The alkyl alkanolamide represented by the following formula (9) may be used.

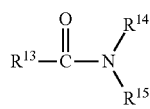

(9)

wherein $R^{13}$ represents a linear chain or branched chain saturated or unsaturated hydrocarbon group having 5 to 23 carbon atoms, $R^{14}$ and $R^{15}$ each independently represent a hydrogen atom or an alkanol group having 1 to 4 carbon atoms, provided that the case where $R^{14}$ and $R^{15}$ are a hydrogen atom at the same time is excluded.

The number of carbon atoms of $R^{13}$ is, from the viewpoints of foaming of the hair dye and the solubility of the dye contained in the hair dye, preferably 8 to 22, further preferably 10 to 20, and further preferably 12 to 18.

Specific examples of the alkyl alkanolamide include coconut oil fatty acid monoethanolamide, coconut oil fatty acid diethanolamide, lauric acid isopropanolamide, and oleic acid diethanolamide.

Polyoxyalkylene alkylamine represented by the following formula (10) may be used.

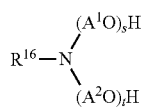

(10)

wherein $R^{16}$ represents a linear chain or branched chain saturated or unsaturated hydrocarbon group having 5 to 23 carbon atoms, $A^1$ and $A^2$ each independently represent an ethylene group or a propylene group, s and t are each an average value and the total of both is 5 to 50.

The number of carbon atoms of $R^{16}$ is, from the viewpoints of foaming of the hair dye and the solubility of the dye contained in the hair dye, preferably 8 to 22, further preferably 10 to 20, and further preferably 12 to 18. $A^1$ and $A^2$ are preferably an ethylene group. The total of s and t is preferably 8 to 30, and more preferably 10 to 20.

Specific examples of the polyoxyalkylene alkylamine include polyoxyethylene lauryl amine, polyoxyethylene cetyl amine, and polyoxyethylene cocamine.

Alkyl polyglucoside preferably has an alkyl group having 6 to 22 carbon atoms and a degree of condensation of the glucoside unit of 1 to 7. Specific examples include octylpolyglucoside, 2-ethylhexyl polyglucoside, decyl polyglucoside, lauryl polyglucoside, myristyl polyglucoside, palmityl polyglucoside, isostearyl polyglucoside, stearyl lauryl polyglucoside, oleyl polyglucoside, and behenyl polyglucoside. Of these, those having an alkyl group having 8 to 18 carbon atoms and a degree of condensation of the glucoside unit of 1 to 7 are preferable.

Alkyl glyceryl ether is preferably those wherein the alkyl group has preferably 8 to 20 carbon atoms, further preferably 14 to 18, and is a branched chain alkyl group. Specific examples include isostearylglyceryl ether, and isostearylpentaerythryl glyceryl ether.

Of these nonionic surfactants, polyoxyalkylene alkyl ether is preferable from the viewpoints of the stability of the hair dye and the solubility of the dye contained in the hair dye.

Two or more of the nonionic surfactants may be used in combination. A content of the nonionic surfactant in the mixed solution is, from the viewpoint of suitable foam retention, preferably 1 mass % or more, more preferably 1.5 mass % or more, further preferably 2 mass % or more, and further preferably 5 mass % or more, and is preferably 35 mass % or less, more preferably 30 mass % or less, further preferably 25 mass % or less, and further preferably 20 mass % or less. A content of the nonionic surfactant in the first agent is, from the viewpoint of good solubility of the dye, preferably 1 mass % or more, more preferably 1.5 mass % or more, and further preferably 5 mass % or more, and is preferably 30 mass % or less, more preferably 25 mass % or less, and further preferably 20 mass % or less.

A mass ratio of the nonionic surfactant to the cationic surfactant (a content of the nonionic surfactant/a content of the cationic surfactant) in the mixed solution is, from the viewpoints of applicability of the hair dye and the foam retention, preferably 2 or more, more preferably 3 or more, further preferably 5 or more, and further preferably 7 or more, and is preferably 50 or less, more preferably 30 or less, further preferably 20 or less, and further preferably 12 or less.

[Amphoteric Surfactant]

The cosmetic product for hair bleaching or hair dyeing of the present invention may further contain an amphoteric surfactant in either one of the first agent or the second agent or in both of the parts.

Examples of the amphoteric surfactant include surfactants of carbobetaine type having an alkyl group having 8 to 24 carbon atoms, an alkenyl group, or an acyl group, amidobetaine type, sulfobetaine type, hydroxysulfobetaine type, amidosulfobetaine type, phosphobetaine type, imidazolinium type, and amine oxide type, of which carbobetaine surfactants, sulfobetaine surfactants are preferable. Preferable amphoteric surfactants include lauramidopropyl betaine, cocamidopropyl betaine, lauryl dimethylaminoacetic acid betaine, and lauryl hydroxy sulfobetaine.

A content of the amphoteric surfactant in the mixed solution of the first agent and the second agent is, from the viewpoint of good foaming, preferably 0.01 mass % or more, and more preferably 0.1 mass % or more, and is preferably 20 mass % or less, more preferably 15 mass % or less, and further preferably 10 mass % or less.

[Dye]

When the cosmetic product for hair bleaching or hair dyeing of the present invention is the hair dye cosmetic product, the first agent contains an oxidation dye intermediate or a direct dye.

(Oxidation Dye Intermediate)

As the oxidation dye intermediate, a known precursor and coupler which are commonly used in hair dyes can be used. Examples of the precursor include paraphenylenediamine, toluene-2,5-diamine, orthochloroparaphenylenediamine, N-phenylparaphenylenediamine, N,N-bis(hydroxyethyl)

paraphenylenediamine, 3-methyl-4-aminophenol, 2-hydroxyethylparaphenylenediamine, paraaminophenol, paramethylaminophenol, 4-amino-metacresol, orthoaminophenol, and salts thereof.

Examples of the coupler include resorcin, 2-methylresorcin, 1-naphthol, 1,5-dihydroxynaphthalene, 5-aminoorthocresol, metaphenylenediamine, orthoaminophenol, metaaminophenol, paraaminophenol, 2,4-diaminophenoxyethanol, 2,6-diaminopyridine, 2-methyl-5-hydroxyethylaminophenol, 2-amino-3-hydroxypyridine, and salts thereof.

Two or more of the precursors and the couplers may each be used in combination, and a content of the precursor and the coupler in the first agent each is preferably 0.01 mass % or more, and more preferably 0.1 mass % or more, and is preferably 5 mass % or less, and more preferably 4 mass % or less.

(Direct Dye)

Examples of the direct dye include acid dyes, nitro dyes, disperse dyes, and basic dyes. More specifically, examples of the acid dye include Blue No. 1, Purple No. 401, Black No. 401, Orange No. 205, Red No. 227, Red No. 106, Yellow No. 203, and Acid Orange No. 3, examples of the nitro dyes include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, NC Yellow 4, HC Yellow 5, HC Red 3, and N,N-bis(2-hydroxyethyl)-2-nitro-p-phenylenediamine, examples of the disperse dye include Disperse Purple 1, Disperse Blue 1, and Disperse Black 9, and examples of the basic dye include Basic Blue 99, Basic Brown 16, Basic Brown 17, Basic Red 76, Basic Yellow 76, Basic Orange 31, and Basic Red 51.

Two or more of the direct dyes may be used in combination or the direct dye may be used in combination with the oxidation dye intermediate. A content of the direct dye in the first agent is preferably 0.001 mass % or more, and more preferably 0.01 mass % or more and is preferably 5 mass % or less, and more preferably 3 mass % or less.

[Oil Agent]

The cosmetic product for hair bleaching or hair dyeing of the present invention can further contain an oil agent from the viewpoint of stabilizing the foam of the mixed solution to be discharged. Examples of such an oil agent include hydrocarbons such as squalene, squalane, liquid paraffin, liquid isoparaffin, and cycloparaffin; glycerides such as castor oil, cacao seed oil, mink oil, avocado oil, and olive oil; waxes such as bees wax, whale wax, lanolin, and carnauba wax; esters such as isopropyl palmit t isopropyl myristate, octyldodecyl myristate, hexyl laurate, cetyl lactate, propylene glycol monostearate, oleyloleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearyl acid, and isopalmitic acid; higher alcohols such as myristyl alcohol, cetyl alcohol, stearyl alcohol, behenyl alcohol, 2-octyldodecanol, and cetostearyl alcohol; and additionally isostearylglyceryl ether, and polyoxypropylenebutyl ether. Of these, higher alcohols are preferable, and further myristyl alcohol, cetyl alcohol, stearyl alcohol, and 2-octyldodecanol are preferable.

A content of the oil agent in the mixed solution of the first agent and the second agent is preferably 0.01 mass % or more, more preferably 0.03 mass % or more, and further preferably 0.05 mass % or more, and is preferably 3 mass % or less, more preferably 2.5 mass % or less, and further preferably 2 mass % or less.

[Silicones]

The cosmetic product for hair bleaching or hair dyeing of the present invention preferably does not contain silicone in the mixed solution of the first agent and the second agent from the viewpoint of retaining the discharged foams for an extended period of time but can further contain silicones within a predetermined range for smoothly blending the foam with hair and imparting high conditioning effects on hair. Examples of the silicones include dimethylpolysiloxane, methylphenyl polysiloxane, polyether modified silicone, amino modified silicone, oxazoline modified silicone elastomer, and emulsions in which these surfactants are dispersed in water. Of these, polyether modified silicone, amino modified silicone, and emulsions thereof are preferable from the viewpoint of stable dispersibility in water without using a thickener.

The polyether modified silicone encompasses those with terminal modification and side-chain modification such as pendant type (comb type), both-ends modified type, and one-end modified type. Examples of such a modified silicone include dimethyl siloxane-methyl(polyoxyethylene)siloxane copolymers, dimethyl siloxane-methyl(polyoxypropylene)siloxane copolymers, and dimethyl siloxane-methyl (polyoxyethylene-polyoxypropylene)siloxane copolymers. The polyether modified silicone is preferably those having an HLB of 10 or more, and further preferably an HLB of 10 to 18, from the viewpoint of the compatibility with water. The HLB used herein is a value determined from a haze value (haze value: an indicator correlative to an HLB and applied to an ether type nonionic surfactant).

The amino modified silicone may be those having an amino group or an ammonium group, but amodimethicone is preferable.

A content of the silicones when added to the mixed solution of the first agent and the second agent is, from the viewpoints of smoothly blending the foam with hair and imparting high conditioning effects on hair, preferably 0.005 mass % or more, and further preferably 0.01 mass % or more, and is, from the viewpoint of not preventing the hair dye from producing the foam, preferably 2 mass % or less, further preferably 1.5 mass % or less, and further preferably 1 mass % or less.

[Nonvolatile Hydrophilic Solvent]

Further, the first agent or the second agent preferably contains a nonvolatile hydrophilic solvent. Such a solvent can relieve the irritation to the scalp caused by the concentrated irritative component such as hydrogen peroxide when the moisture evaporates from the mixed solution while left to stand after the foam of the mixed solution is applied to hair. The nonvolatile hydrophilic solvent is preferably polyols, lower (1 to 4 carbon atoms) alkyl ethers thereof. Polyols are preferably those having 2 to 6 carbon atoms, and examples include glycerol, diglycerol, propylene glycol, dipropylene glycol, 1,3-butanediol, ethylene glycol, diethylene glycol, isoprene glycol, and sorbitol. Examples of the lower alkyl ethers of polyol include mono-lower alkyl ethers and poly-lower alkyl ethers of polyol (e.g., di-lower alkyl ether). Of these, monomethyl ether or monoethyl ether of polyol is preferable, specific examples include ethylene glycol monomethyl ether, ethylene glycol monoethyl ether, diethylene glycol monomethyl ether, and diethylene glycol monoethyl ether. Two or more of these may be used in combination.

A content of the nonvolatile hydrophilic solvent in the mixed solution of the first agent and the second agent is, from the viewpoints of reducing effects of the scalp irritation and effects for providing good foam quality, preferably 0.1 mass % or more, more preferably 0.3 mass % or more, further preferably 0.5 mass % or more, and further preferably 1 mass % or more, and is preferably 10 mass % or less, more preferably 5 mass % or less, further preferably 3 mass % or less, and further preferably 2 mass % or less.

[Other Optional Components]

The cosmetic product for hair bleaching or hair dyeing of the present invention can contain other components commonly used as cosmetic ingredients in addition to the above components. Examples of such an optional component include animal and vegetable oils and fats, natural or synthetic polymers, ethers, protein derivatives, hydrolyzed proteins, amino acids, preservatives, chelating agents, stabilizers, antioxidants, plant extracts, crude drug extracts, vitamins, perfumes, and UV absorbers.

[pH]

In the cosmetic product for hair bleaching or hair dyeing of the present invention, pH (25° C.) of the mixture is, from the viewpoints of hair dyeing effects and skin irritation, preferably 8 or more, and more preferably 9 or more, and is preferably 12 or less, more preferably 11 or less, and further preferably 10.5 or less. Examples of the pH control agents include, in addition to the above alkali agents, inorganic acids such as hydrochloric acid and phosphoric acid; organic acids such as citric acid, glycolic acid, and lactic acid; phosphates such as monopotassium dihydrogenphosphate and disodium monohydrogenphosphate.

[Viscosity]

The range of a viscosity of the mixed solution of the first agent and the second agent is preferably 1 mPa·s or more, and more preferably 10 mPa·s or more, and is preferably 600 mPa·s or less, more preferably 300 mPa·s or less, further preferably 200 mPa·s or less, and further preferably 100 mPa·s or less. The viscosity used herein is measured at 25° C. with a B type rotational viscometer (model; a digital viscometer TV-10, Toki Sangyo Co., Ltd.) using rotor No. 1 at a rotational speed of 60 rpm when the subject to be measured is 100 mPa·s or less, 30 rpm when the subject to be measured is 100 to 200 mPa·s, and 12 rpm when the subject to be measured is 200 mPa·s or more. The measurement is carried out in order of decreasing number of rotation and is completed when the measurement can be carried out without going off scale, and the measurement thereafter with smaller numbers of rotation is not carried out. The viscosity of the mixed solution is set to be measured after 3 minutes have passed since the mixing of each of the parts started.

The viscosity of the mixed solution of the first agent and the second agent adjusted to the above range can achieve an easily applicable foam volume and also prevent the mixed solution from dripping after applied to hair. The adjusted viscosity also provides easy squeezing when discharging the foam from a squeeze foamer and easy pumping when discharging the foam from a pump foamer. For adjusting the viscosity of the mixed solution to the above range, a water soluble solvent may be added or a content and kind of a surfactant, polyols, a higher alcohol, and the like may suitably be adjusted.

[Foamer Container]

In the present invention, the foamer container is a nonaerosol type container and used for mixing the mixed solution of the first agent and the second agent with air without using propellant and discharging the solution in the form of foam. The use of a foamer container provides an effect to prevent the discharged parts from splashing and another effect to discharge the foam in which the first agent and the second agent are homogeneously mixed. Particularly, the nonaerosol type container can be produced at a lower cost than aerosol type containers and are safer to handle in the distribution as a high-pressure gas propellant is not required.

Examples of the foamer container which can be used include known pump foamer containers, squeeze foamer containers, electric mixers, and accumulator pump foamer containers, all of which have foam discharging means. More specifically, examples include the pump foamer E3 type, F2 type of the same product (Daiwa Can Company), squeeze foamers (Daiwa Can Company), electric mixers (Matsushita Electric Works), and airspray foamers (Airspray International Inc.) described in "FOOD & PACKAGING" (vol. 35, No: 10, p 588-593 (1994); vol. 35, No. 11, p 624-627 (1994); vol. 36, No. 3, p 154-158 (1995)). The foamer container used for the cosmetic product for hair bleaching or hair dyeing of the present invention is preferably a pump foamer container or a squeeze foamer container due to a lower price and easy use.

The pump foamer container or the squeeze foamer container has a foam producing portion such as a net, and is preferably provided with a thin net for solving a clogging, which is caused when the mixed solution of the first agent and the second agent is dried and solidified, by immediately dissolving the solidified product using a foam flow at next discharge. In this instance, the net mesh is preferably 50 to 280 mesh, further preferably 90 to 250 mesh, and further preferably 130 to 22 mesh. The mesh used herein is the number of meshes per inch. The use of a net having the mesh within this range can produce a creamy foam. Preferable examples of the material for such a mesh include nylon and polyester.

The foamer container used for the cosmetic product for hair bleaching or hair dyeing of the present invention is provided with at least one sheet, preferably more than one sheet, of such a net, and particularly preferably two sheets from the viewpoints of the economic efficiency and foam stability.

The foamer container is preferably composed of a material, which is not corroded by alkali or hydrogen peroxide for the portions contacting the content (the inner walls of the container, the inner walls of the foam discharging means, and the like) and allows oxygen generated by the decomposition of hydrogen peroxide to pass through.

The cosmetic product for hair bleaching or hair dyeing of the present invention, provided with the first agent, the second agent, and the foamer container, may be in the production form in which the first agent and the second agent are each packed in a separate container from the foamer container and both parts are transferred to the foamer container and mixed upon application, but may also be in the production form in which either one of the parts is packed in the foamer container, the other agent is packed in a separate container, and the other agent is transferred to the foamer container upon application. In this instance, the second agent is preferably packed in a gas permeable container, particularly in a foamer container composed of an oxygen permeable material (e.g., polyethylene), for preventing a pressure inside the container from increasing due to the oxygen generated by the decomposition of hydrogen peroxide. On the other hand, the first agent requires a container, which hardly allows oxygen to pass through, for preventing the oxidation of the oxidation dye.

A mixing ratio of the first agent and the second agent in the cosmetic product for hair bleaching or hair dyeing of the present invention is, on a mass ratio basis, preferably 1:4 to 4:1, and further preferably 1:3 to 1:2.

[Gas-Liquid Mixing Ratio]

A gas-liquid mixing ratio of air and the mixed solution by the foam discharging means of the foamer container is, from the viewpoints of easy blendability and easy applicability of the parts to hair, preferably 5 mL/g or more, and more preferably 8 mL/g or more, and is preferably 40 mL/g or less, and more preferably 30 mL/g or less. The gas-liquid mixing ratio used herein is the value measured as follows.

First, a mass and a volume of the foam discharged at 25° C. are measured to determine a gas-liquid mixing ratio. 100 g of the mixed solution is put in a squeeze foamer container (Daiwa Can Company, a volume 210 mL, mesh coarseness (aperture) 150 mesh (150 squares per inch (25.4 mm) in the mixing chamber, 200 mesh in the tip), 20 g of the foam is discharged into a 1,000 mL-graduated cylinder when a balance is 80 g, and a foam volume is measured 1 minute later from the start of discharging. A gas-liquid mixing ratio (mL/g) is determined by dividing the discharged foam volume (mL) by a mass of 20 g.

[How to Use]

For bleaching or dyeing hair (particularly the hair of the head) using the cosmetic product for hair bleaching or hair dyeing of the present invention, it is preferable to comb hair in advance. Combing hair helps avoid tangled hair during the re-foaming treatment to be described later and prevents the mixed solution from splashing. After combing hair, the blocking operation commonly used when a bleach or hair dye composition is applied is not required, further the blocking operation is preferably not carried out. Thus, the application operation of the bleach or hair dye composition to hair and the re-foaming operation to be described later become easier. The re-foaming operation can achieve far better even color finishing even when the cosmetic product for hair bleaching or hair dyeing of the present invention is applied to hair with a hair styling product left thereon. Then, the first agent and the second agent of the cosmetic product for hair bleaching or hair dyeing of the present invention are mixed in the foamer container. The foamy agent discharged from the container may be applied directly to hair or applied to hair using a tool such as a hand or a brush. It is more preferable to first take the foamy agent in the (gloved) hand and subsequently apply it to hair from the viewpoints of preventing the agent from splashing or dripping.

After applied, the foamy agent is allowed to stand for about 3 to 60 minutes, and preferably about 5 to 45 minutes. During this time, it is preferable to re-foam the foamy agent on hair from the viewpoints of further preventing the dripping while waiting and sufficiently spreading the mixed solution throughout the entire hair roots. Re-foaming may be achieved by injecting a gas, using equipment such as a vibrator or a brush, or using fingers, but using fingers is more preferable.

The timing of re-foaming may be after the foam thoroughly disappeared, while the foam is disappearing, or before the applied foam transforms. Alternatively, such a timing may also be after completing the application of foam throughout the entire area of intention or in the middle of the application. Re-foaming may be carried out in a single continuous procedure or intermittently repeated more than once.

After such an operation, the mixed solution is washed away. Subsequently, shampooing and rinsing are appropriately carried out, hair is washed with water and dried.

A specific method for bleaching or dyeing hair using the cosmetic product for hair bleaching or hair dyeing of the present invention is preferably the method comprising the following steps (1) to (4).

(1) a step of preparing the mixed solution by mixing the first agent comprising an alkali agent and the second agent comprising hydrogen peroxide in the container body of a nonaerosol foamer container;

(2) a step of discharging the mixed solution prepared in the step (1) as a foamy substance from the nonaerosol foamer container after attaching a nonaerosol foamer to the container body;

(3) a step of applying the foamy substance to hair with a hand; and (4) a step of rubbing the foamy substance on hair with a hand to achieve an average foam diameter of 100 μm or less of the foamy substance.

[Step (1)]

The step (1) is a step of preparing the mixed solution by mixing the first agent comprising an alkali agent and the second agent comprising hydrogen peroxide in the container body of a nonaerosol foamer container.

For the preparation of the mixed solution, the first agent and the second agent may each be packed in a container separate from the container body of the foamer container until application and both of the parts may be transferred to the container body and mixed upon application, but alternatively one of the parts may be packed in the container body of the foamer container until application and the other agent is packed in a separate container, and the other agent may be transferred to the container body of the foamer container upon application. In this instance, the second agent is preferably packed in a gas permeable container, more preferably in a container composed of an oxygen permeable material (e.g., polypropylene or polyethylene), for preventing a pressure inside the container from increasing due to the oxygen generated by the decomposition of hydrogen peroxide. On the other hand, the first agent requires a container, which hardly allows oxygen to pass through, for preventing the oxidation of the oxidation dye.

[Step (2)]

The step (2) is a step of discharging the mixed solution prepared in the step (1) as a foamy substance from the nonaerosol foamer container after attaching a nonaerosol foamer to the container body.

A volume of the foamy substance after discharged (before applied) is, from a viewpoint of covering the entire head with the foamy substance, preferably 900 mL or more, and more preferably 1,000 mL or more, and is preferably 2,000 mL or less, more preferably 1,800 mL or less, and further preferably 1,500 mL or less.

An average foam diameter of the foamy substance after discharged (before applied) is, from the viewpoint of preventing dripping, preferably 110 μm or more, and is preferably 300 μm or less, more preferably 250 μm or less, and further preferably 200 μm or less.

In the present invention, for determining the average foam diameter of the foamy substance, the foam was moved to a glass petri dish and photographed within 1 minute from the back of the glass petri dish using a microscope with 230× magnifications. The longest portions of ten foams randomly selected from the photographed image were measured as the diameters and the average thereof was defined as the average foam diameter.

A viscosity (25° C.) of the foamy substance after discharged (before applied) is, from the viewpoint of preventing the dripping, preferably 5,000 mPa·s or more, more preferably 7,000 mPa·s or more, and is, from the viewpoint of easy spreadability, preferably 15,000 mPa·s or less, more preferably 12,000 mPa·s or less, and further preferably 10,000 mPa·s or less.

In the present invention, the viscosity (25° C.) of the foamy substance is a value (T-C bar, measured at 10 rpm for 1 minute) measured using a helical viscometer (TVB-10R, product of Toki Sangyo Co., Ltd.).

A foam complex modulus of elasticity (25° C.) after discharged (before applied) is preferably 150 Pa or more, more preferably 180 Pa or more, and further preferably 200 Pa or more, and is preferably 500 Pa or less, more preferably 400 Pa or less, and further preferably 350 Pa or less.

When a pump foamer container is used to be the nonaerosol foamer container, the foamy substance is discharged by pressing down the pump foamer with the palm, whereas when a squeeze foamer container is used, the foamy substance can be discharged by squeezing the container body with a hand.

[Step (3)]

The step (3) is a step of applying the foamy substance to hair with a hand.

When applying the foamy substance to hair with a hand, the liquid component contained in the foamy substance is absorbed into hair and as a result the first foamy substance applied to hair is liable to disappear. Therefore, for retaining the foamy substance on hair, it is preferable to apply the foamy substance twice or more, further preferably three to five times, on the same place.

A volume of the foamy substance present on hair at the time of completing the application (before rubbing) is, from the viewpoint of covering the entire head with the foamy substance, preferably 200 mL or more, more preferably 250 mL or more, and further preferably 300 mL or more, and is preferably 800 mL or less, and more preferably 600 mL or less.

An average foam diameter of the foamy substance present on hair after completing the application (before rubbed) is, from the viewpoint of preventing dripping, preferably 200 µm or less, and more preferably 150 µm or less.

A foam complex modulus of elasticity (25° C.) at the time of completing the application (before rubbing) is, from the viewpoint of preventing the dripping, preferably 200 Pa or more, more preferably 350 Pa or more, and further preferably 400 Pa or more.

In the step (3), it is preferable to apply the foamy substance to hair with a gloved hand from the viewpoint of protecting the hand.

Before the step (3), combing hair in advance is preferable. Combing hair helps avoid tangled hair in the subsequent step (4), allowing reduction in the possibility of splashing the mixed solution. In addition, after combing hair, the blocking operation commonly used when the conventional hair dye or bleach composition is applied is not required, and further the blocking operation is preferably not carried out. Thus, operations of the subsequent step (4) and thereafter can be easily proceeded.

[Step (4)]

The step (4) is a step of rubbing the foamy substance on hair with a hand to achieve an average foam diameter of 100 µm or less of the foamy substance. Such a step (4) enables the obtention of the foamy composition, which closely contacts the hairline.

An average foam diameter of the foamy substance after rubbed is, from the viewpoint of improving the close contact properties of the foamy substance at the hairline, preferably 30 µm or more, and more preferably 50 µm or more, and is preferably 90 µm or less, more preferably 80 µm or less, and further preferably 70 µm or less.

When an average foam diameter of the foamy substance after rubbed at this point does not reach the above ranges, a desired average foam diameter range may also be achieved by applying a thickener to hair. Thus, the close contact properties of the foamy substance to hair can be improved.

A foam complex modulus of elasticity (25° C.) after rubbed is, from the viewpoint of improving the close contact properties of hair by the foamy substance, preferably 800 Pa or more, more preferably 950 Pa or more, and further preferably 1,100 Pa or more, and is preferably 2,000 Pa or less, more preferably 1,700 Pa or less, and further preferably 1,600 Pa or less.

By rubbing, the liquid content of the foamy substance is sheared while absorbed in hair and fine precipitates grow in the foam films by the interaction between the anionic surfactant and the cationic surfactant. The precipitates when staying in the gas-liquid interface such as Plateau border of the foams cause difficult drainage and prevent the foam unification. Thus, it is presumed that a shear force applied from rubbing consequently increases a foam complex modulus of elasticity, whereby the foams change to contact closely.

After rubbing the foamy substance on hair, a volume of the foamy substance present on hair is, from the viewpoint of covering the entire head with the foamy substance, preferably 200 mL or more, more preferably 250 mL or more, and further preferably 300 mL or more, and is preferably 800 mL or less, more preferably 600 mL or less, and further preferably 580 mL or less.

Rubbing the foamy substance on hair for a longer time can reduce an average foam diameter of the foamy substance. The time for rubbing the foamy substance on hair is, from the viewpoints of evaporating water and reducing an average foam diameter, preferably 2 to 10 minutes, more preferably 3 to 10 minutes, and further preferably 5 to 10 minutes.

[Step (5)]

Further, after rubbing the foamy substance on hair in the step (4), as the step (5), a step of smoothing hair at the hairline while pressing down to the scalp to condition hair not to detach can be added. Thus, the step (5) enables the obtention of the foamy composition by which hair does not detach.

When hair at the hairline is smoothed while pressed down to the scalp to create the condition in which hair does not detach, the close contact properties of the foamy substance at the hairline can be improved.

Further, during this procedure, it is preferable to smooth hair backward. By this motion, hair is conditioned not to detach due to the foamy substance and consequently a condition can be created in which the close contact properties of the foamy substance on hair is further improved with no detached hair present.

[Step (6)]

As the step (6), a step of collecting the foamy substance present on hair to the hairline area can be added after the step (4) or (5).

With such a step, hairs at the hairline closely contact with each other and at the same time tresses of hair at the hairline are effectively prevented from being detached. As a result, the effects of the present invention, that is, hair can be evenly dyed or bleached from the tips to roots of the hairs, can further be enhanced.

[Other Steps]

The method for dyeing or bleaching hair of the present invention can further include, after the step (4), (5), or (6), a step of leaving the foamy substance to stand for 3 to 60 minutes and a step of washing the foamy substance on hair away with water.

With regard to the present embodiments described above, preferable aspects of the present invention are further disclosed below.

<1> A cosmetic product for hair bleaching or hair dyeing comprising a first agent comprising an alkali agent, a second agent comprising hydrogen peroxide, and a nonaerosol foamer container for discharging a mixed solution of the first agent and the second agent in the form of foam, the mixed solution comprising the following components (A) to (C).
(A) a anionic surfactant comprising sulfuric acid group,
(B) a anionic surfactant comprising carboxy group, and
(C) a polymer comprising a diallyl quaternary ammonium salt as a constitutional unit and having a charge density of 5.5 meq/g or more and 8.0 meq/g or less.

<2> The cosmetic product for hair bleaching or hair dyeing according to <1>, wherein a mass ratio of the components (A) and (B) in total to the component (C), [(A)+(B)]/(C), in the mixed solution is preferably 0.1 or more, more preferably 0.5 or more, further preferably 1 or more, further preferably 1.5 or more, further preferably 2 or more, and further preferably 3 or more, and is preferably 15 or less, more preferably 12 or less, further preferably 10 or less, and further preferably 5 or less.

<3> The cosmetic product for hair bleaching or hair dyeing according to <1> or <2> wherein a content of the component (A) in the mixed solution is preferably 0.01 mass % or more, more preferably 0.1 mass % or more, further preferably 0.5 mass % or more, and further preferably 0.7 mass % or more, and is preferably 20 mass % or less, more preferably 10 mass % or less, further preferably 5 mass % or less, further preferably 3 mass % or less, further preferably 2 mass % or less, and further preferably 1.5 mass % less.

<4> The cosmetic product for hair bleaching or hair dyeing according to any of <1> to <3>, wherein a content of the component (B) in the mixed solution is preferably 0.01 mass % or more, more preferably 0.1 mass % or more, further preferably 0.5 mass % or more, and further preferably 0.7 mass % or more, and is preferably 20 mass % or less, more preferably 10 mass % or less, further preferably 7 mass % or less, further preferably 5 mass % or less, further preferably 3 mass % or less, and further preferably 2 mass % or less.

<5> The cosmetic product for hair bleaching or hair dyeing according to any of –1> to <4>, wherein a content of the component (C) in the mixed solution is preferably 0.01 mass % or more, more preferably 0.1 mass % or more, and further preferably 0.3 mass % or more, and is preferably 20 mass % or less, more preferably 10 mass % or less, further preferably 5 mass % or less, further preferably 3 mass % or less, and further preferably 1.5 mass % or less.

<6> The cosmetic product for hair bleaching or hair dyeing according to any of <1> to <5>, wherein a content of the components (A) and (B) in total in the mixed solution is preferably 0.02 mass % or more, more preferably 0.2 mass % or more, further preferably 0.5 mass % or more, and further preferably 1 mass % or more, and is preferably 20 mass % or less, more preferably 10 mass % or less, further preferably 7 mass % or less, further preferably 5 mass % or less, further preferably 3 mass % or less, and further preferably 2.5 mass % or less.

<7> The cosmetic product for hair bleaching or hair dyeing according to any of <1> to <6>, wherein the component (A) is preferably a sulfuric acid group comprising surfactant represented by the following formula (1).

$$R\text{—}O\text{—}(CH_2CH_2O)_n\text{—}[CH_2CH(CH_3)O]_m\text{—}SO_3M \tag{1}$$

wherein R represents a hydrocarbon group having 8 to 25 carbon atoms, n represents an average number of moles added of 0 to 50, m represents an average number of moles added of 0 to 50, and M represents an alkali metal atom or $NH_4$.

<8> The cosmetic product for hair bleaching or hair dyeing according to any of <1> to <7>, wherein the component (B) is preferably at least one selected from the group consisting of N-acylamino acid salts, N-acyl-N-alkylamino acid salts, amide type N-acylamino acid salts, ether carboxylates, fatty acid salts, and salts of alkylsuccinic acid, and salts of alkenylsuccinic acid.

<9> The cosmetic product for hair bleaching or hair dyeing according to any of <1> to <8>, wherein a charge density of the component (C) is preferably 5.7 meq/g or more, more preferably 5.9 meq/g or more, and further preferably 6.1 meq/g or more, and is preferably 6.5 meq/g or less.

<10> The cosmetic product for hair bleaching or hair dyeing according to any of <1> to <9>, preferably further comprising a cationic surfactant as a component (D).

<11> The cosmetic product for hair bleaching or hair dyeing according to <10>, wherein the component (D) is preferably those represented by the following formula (6).

wherein $R^7$, $R^8$, $R^9$, and $R^{10}$ each independently represent a hydrocarbon group optionally having a substituent, one or two of $R^7$, $R^8$, $R^9$ and $R^{10}$ have 8 to 36 carbon atoms, and the remainder has 1 to 7 carbon atoms, and $X^-$ represents an anion.

<12> The cosmetic product for hair bleaching or hair dyeing according to <10> or <11>, wherein a content of the component (D) in the mixed solution is preferably 0.05 mass % or more, more preferably 0.2 mass % or more, and further preferably 0.4 mass % or more, and is preferably 5 mass % or less, more preferably 4 mass % or less, and further preferably 3 mass % or less.

<13> The cosmetic product for hair bleaching or hair dyeing according to any of <1> to <12>, preferably further comprising a higher alcohol as a component (E).

<14> The cosmetic product for hair bleaching or hair dyeing according to <13>, wherein the component (E) is preferably those represented by the following formula (7).

$$R^{11}\text{—}OH \tag{7}$$

wherein $R^{11}$ is a linear chain or branched chain hydrocarbon group having 12 to 24 carbon atoms.

<15> The cosmetic product for hair bleaching or hair dyeing according to <13> or <14>, wherein a content of the component (E) in the mixed solution is preferably 0.05 mass % or more, more preferably 0.2 mass % or more, and further preferably 0.4 mass % or more, and is preferably 5 mass % or less, more preferably 4 mass % or less, and further preferably 3 mass % or less.

<16> A method for bleaching or dyeing hair comprising using the cosmetic product for hair bleaching or hair dyeing of any of <1> to <15>, discharging the mixed solution of the first agent and the second agent from the nonaerosol foamer container in the form of foam, and applying the foam to hair with a hand.

<17> A method for dyeing or bleaching hair comprising the following steps (1) to (4).

(1) a step of preparing a mixed solution by mixing a first agent comprising an alkali agent and a second agent comprising hydrogen peroxide in the container body of a nonaerosol foamer container;

(2) a step of discharging the mixed solution prepared in the step (1) as a foamy substance from the nonaerosol foamer container after attaching a nonaerosol foamer to the container body;

(3) a step of applying the foamy substance to hair with a hand; and (4) a step of rubbing the foamy substance on hair with a hand to achieve an average foam diameter of 100 μm or less of the foamy substance.

<18> The method for dyeing or bleaching according to <17>, wherein an average foam diameter of the foamy substance discharged in the step (2) is preferably 110 μm or more, and is preferably 300 μm or less, more preferably 250 μm or less, and further preferably 200 μm or less.

<19> The method for dyeing or bleaching according to <17> or <18>, wherein an average foam diameter of the foamy substance after rubbed with a hand in the step (4) is preferably 30 μm or more, and more preferably 50 μm or more, and is preferably 90 μm or less, more preferably 80 μm or less, and further preferably 70 μm or less.

<20> A method for dyeing or bleaching hair comprising the following steps (1) to (5)

(1) a step of preparing a mixed solution by mixing a first agent comprising an alkali agent and a second agent comprising hydrogen peroxide in the container body of a nonaerosol foamer container (2) a step of discharging the mixed solution prepared in the step (1) as a foamy substance from the nonaerosol foamer container after attaching a nonaerosol foamer to the container body (3) a step of applying the foamy substance to hair with a hand (4) a step of rubbing the foamy substance on hair with a hand; and (5) a step of smoothing hair at the hairline while pressing down to the scalp to create a condition in which hair does not detach.

<21> The method for dyeing or bleaching hair according to <20>, wherein, in the step (5), hair at the hairline is preferably smoothed backward.

<22> The method for dyeing or bleaching according to any of <17> to <21>, preferably further comprising a step of collecting the foamy substance present on hair to the hairline area as a step (6).

EXAMPLES

Examples 1 to 11, Comparative Examples 1 to 2

<Out Bath Treatment Procedure>

Using a black hair (hair of a Chinese person) purchased from Beaulax Co., Ltd., a tress with a length of 27 cm and a weight of 8 g was prepared, and a step was carried out in which the tress was washed once using a shampoo, dried with a towel, 0.05 g of Asience shinayaka bihatsu oiru ("Asience Treatment Oil making the hair supple and beautiful" in English) (Kao Corporation) was applied thereto, and blow-dried.

The first agent and the second agent of the composition formulae shown in Tables 1 to 4 were prepared and mixed in a 1:2 ratio to prepare the mixed solution. The obtained mixed solution was discharged in the form of foam using a squeeze foamer (Daiwa Can Company, a volume of 210 mL, mesh coarseness of 150 mesh in the mixing chamber, 200 mesh in the tip, the total opening area of the narrowest portions in the air introducing channel of 0.35 mm$^2$, an inner diameter of the dip tube of $\phi$ 1.7 mm).

<Evaluation on the Foaming when Applied to Hair Subjected to a Treatment>

7 g of the discharged foamy substance was applied to the 27 cm- and 8 g-tress subjected to a treatment and the foaming when the tress was rubbed with a hand was evaluated based on the following criteria. The evaluation results are shown together in Tables 1 to 4.

4: Elastic, extremely fine-textured foam was formed.
3: Slightly elastic, fine-textured foam was formed.
2: Slightly watery, rather coarse-textured foam was formed.
1: Watery, coarse-textured foam was formed.

<Evaluation of the Foam Volume (Foam Retention) after Applied to Hair Subjected to a Treatment>

7 g of the discharged foamy substance was applied to the 27 cm- and 8 g-tress subjected to a treatment, the tress was rubbed ten times with a hand, and subsequently allowed the foamy substance to be blended with hair (left to stand) for 2 minutes. Then, the foam was rubbed off from hair and a foam volume was measured in a graduated cylinder. The evaluation results are shown together in Tables 1 to 4.

The above evaluation verified that the tress with good foaming and foam retention achieved dyes without causing uneven colors.

*1 to *4 appeared in Tables 1 to 4 are as follows.
*1: Product of Lubrizol Advanced Materials, Inc., Merquat 295, a charge density of 6.0 meq/g (active amount)
*2: Product of Lubrizol Advanced Materials, Inc., Merauat 100, a charge density of 6.2 meq/g (active amount)
*3: Product of Lubrizol Advanced Materials, Inc., Merquat 280, a charge density of 5.0 meq/g (active amount)
*4. Amount for pH control (for pH 3.5±0.05)

TABLE 1

|  | Example | | | |
| --- | --- | --- | --- | --- |
| (Mass %) | 1 | 2 | 3 | 4 |
| First agent | | | | |
| Tetrasodium edetate dihydrate | 0.10 | 0.10 | 0.10 | 0.10 |
| Ascorbic acid | 0.40 | 0.40 | 0.40 | 0.40 |
| Sodium sulfite | 0.48 | 0.48 | 0.48 | 0.48 |
| Purified water | Balance | Balance | Balance | Balance |
| Toluene-2,5-diamine | 0.40 | 0.40 | 0.40 | 0.40 |
| Para-aminophenol | 0.10 | 0.10 | 0.10 | 0.10 |
| Resorcin | 0.30 | 0.30 | 0.30 | 0.30 |

TABLE 1-continued

|  | (Mass %) | Example 1 | Example 2 | Example 3 | Example 4 |
|---|---|---|---|---|---|
|  | Meta-aminophenol | 0.10 | 0.10 | 0.10 | 0.10 |
|  | 2,4-Diaminophenoxyethanol hydrochloride | 0.05 | 0.05 | 0.05 | 0.05 |
| (A) | Sodium polyoxyethylene laurylether sulfate | 2.16 | — | 2.16 | 1.35 |
| (A) | Sodium lauryl sulfate | — | 3.00 | — | — |
| (B) | Sodium cocoyl glutamate | 2.42 | 2.42 | 2.42 | 1.21 |
| (B) | Sodium polyoxyethylene(4.5)laurylether acetate | — | — | — | — |
|  | Polyoxyethylene alkyl(12-14) ether | 15.00 | 15.00 | 15.00 | 15.00 |
|  | Myristyl alcohol | 0.30 | 0.30 | 0.30 | 0.30 |
| (C) | Dimethyldiallylammonium chloride-acrylic acid (95:5) copolymer (*1) | 1.20 | 1.20 | — | 2.00 |
| (C) | Polychlorinated dimethylmethylene piperidinium (*2) | — | — | 0.60 | — |
|  | Dimethyldiallylammonium chloride-acrylic acid (65:35) copolymer (*3) | — | — | — | — |
|  | Ethanolamine | 5.00 | 5.00 | 5.00 | 5.00 |
|  | Ethanol | 5.00 | 5.00 | 5.00 | 5.00 |
|  | Total | 100 | 100 | 100 | 100 |
|  | Second agent |  |  |  |  |
|  | Cetyltrimethylammonium chloride | 0.57 | 0.57 | 0.57 | 0.57 |
|  | Stearyltrimethylammonium chloride | 0.19 | 0.19 | 0.19 | 0.19 |
| (A) | Sodium polyoxyethylene laurylether sulfate | — | — | — | — |
| (B) | Sodium cocoyl glutamate | — | — | — | — |
|  | Polyoxyethylene cetyl ether | 0.80 | 0.80 | 0.80 | 0.80 |
|  | Cetanol | 0.50 | 0.50 | 0.50 | 0.50 |
|  | Behenyl alcohol | 0.70 | 0.70 | 0.70 | 0.70 |
|  | Oxyquinoline sulfate | 0.04 | 0.04 | 0.04 | 0.04 |
|  | Hydroxyethanediphosphonic acid | 0.04 | 0.04 | 0.04 | 0.04 |
|  | Sodium hydroxide solution (48 mass %), phosphoric acid (75 mass %) | (*4) | (*4) | (*4) | (*4) |
|  | Hydrogen peroxide (35 mass %) | 16.30 | 16.30 | 16.30 | 16.30 |
|  | Propylene glycol | 0.50 | 0.50 | 0.50 | 0.50 |
|  | Soft lanolin fatty acid | 0.05 | 0.05 | 0.05 | 0.05 |
|  | Purified water | Balance | Balance | Balance | Balance |
|  | Total | 100 | 100 | 100 | 100 |
|  | Mixed solution of first agent and second agent |  |  |  |  |
|  | (A) | 0.72 | 1 | 0.72 | 0.45 |
|  | (B) | 0.81 | 0.81 | 0.81 | 0.4 |
|  | (C) | 0.4 | 0.4 | 0.2 | 0.67 |
|  | [(A) + (B)]/(C) | 3.82 | 2.02 | 7.63 | 1.28 |
|  | Evaluation on the foaming when applied to hair subjected to a treatment | 4 | 4 | 4 | 3 |
|  | Foam volume after applied to hair subjected to a treatment (mL) | 65 | 70 | 53 | 20 |

TABLE 2

|  | (Mass %) | Example 5 | Example 6 | Example 7 | Example 8 |
|---|---|---|---|---|---|
|  | First agent |  |  |  |  |
|  | Tetrasodium edetate dihydrate | 0.10 | 0.10 | 0.10 | 0.10 |
|  | Ascorbic acid | 0.40 | 0.40 | 0.40 | 0.40 |
|  | Sodium sulfite | 0.48 | 0.48 | 0.48 | 0.48 |
|  | Purified water | Balance | Balance | Balance | Balance |
|  | Toluene-2,5-diamine | 0.40 | 0.40 | 0.40 | 0.40 |
|  | Para-aminophenol | 0.10 | 0.10 | 0.10 | 0.10 |
|  | Resorcin | 0.30 | 0.30 | 0.30 | 0.30 |
|  | Meta-aminophenol | 0.10 | 0.10 | 0.10 | 0.10 |
|  | 2,4-Diaminophenoxyethanol hydrochloride | 0.05 | 0.05 | 0.05 | 0.05 |
| (A) | Sodium polyoxyethylene laurylether sulfate | 1.35 | 2.16 | — | — |
| (A) | Sodium lauryl sulfate | — | — | — | — |
| (B) | Sodium cocoyl glutamate | — | 2.42 | — | — |
| (B) | Sodium polyoxyethylene(4.5)laurylether acetate | 9.00 | — | — | — |
|  | Polyoxyethylene alkyl(12-14) ether | 15.00 | 15.00 | 15.00 | 15.00 |
|  | Myristyl alcohol | 0.30 | 0.30 | 0.30 | 0.30 |
| (C) | Dimethyldiallylammonium chloride-acrylic acid (95:5) copolymer (*1) | 1.20 | 0.40 | 1.20 | 1.20 |
| (C) | Polychlorinated dimethylmethylene piperidinium (*2) | — | — | — | — |
|  | Dimethyldiallylammonium chloride-acrylic acid (65:35) copolymer (*3) | — | — | — | — |
|  | Ethanolamine | 5.00 | 5.00 | 5.00 | 5.00 |
|  | Ethanol | 5.00 | 5.00 | 5.00 | 5.00 |
|  | Total | 100 | 100 | 100 | 100 |

TABLE 2-continued

|  | (Mass %) | Example 5 | Example 6 | Example 7 | Example 8 |
|---|---|---|---|---|---|
|  | Second agent |  |  |  |  |
|  | Cetyltrimethylammonium chloride | 0.57 | 0.57 | 0.57 | — |
|  | Stearyltrimethylammonium chloride | 0.19 | 0.19 | 0.19 | — |
| (A) | Sodium polyoxyethylene laurylether sulfate | — | — | 1.35 | 1.35 |
| (B) | Sodium cocoyl glutamate | — | — | 1.69 | 1.69 |
|  | Polyoxyethylene cetyl ether | 0.80 | 0.80 | 0.80 | 0.80 |
|  | Cetanol | 0.50 | 0.50 | 0.50 | 0.50 |
|  | Behenyl alcohol | 0.70 | 0.70 | 0.70 | 0.70 |
|  | Oxyquinoline sulfate | 0.04 | 0.04 | 0.04 | 0.04 |
|  | Hydroxyethanediphosphonic acid | 0.04 | 0.04 | 0.04 | 0.04 |
|  | Sodium hydroxide solution (48 mass %), phosphoric acid (75 mass %) | (*4) | (*4) | (*4) | (*4) |
|  | Hydrogen peroxide (35 mass %) | 16.30 | 16.30 | 16.30 | 16.30 |
|  | Propylene glycol | 0.50 | 0.50 | 0.50 | 0.50 |
|  | Soft lanolin fatty acid | 0.05 | 0.05 | 0.05 | 0.05 |
|  | Purified water | Balance | Balance | Balance | Balance |
|  | Total | 100 | 100 | 100 | 100 |
|  | Mixed solution of first agent and second agent |  |  |  |  |
|  | (A) | 0.45 | 0.72 | 0.9 | 0.9 |
|  | (B) | 3 | 0.81 | 1.13 | 1.13 |
|  | (C) | 0.4 | 0.13 | 0.4 | 0.4 |
|  | [(A) + (B)]/(C) | 1.13 | 11.45 | 5.07 | 5.07 |
|  | Evaluation on the foaming when applied to hair subjected to a treatment | 3 | 3 | 4 | 4 |
|  | Foam volume after applied to hair subjected to a treatment (mL) | 30 | 25 | 70 | 45 |

TABLE 3

|  | (Mass %) | Example 9 | Example 10 | Example 11 |
|---|---|---|---|---|
|  | First agent |  |  |  |
|  | Tetrasodium edetate dihydrate | 0.10 | 0.10 | 0.10 |
|  | Ascorbic acid | 0.40 | 0.40 | 0.40 |
|  | Sodium sulfite | 0.48 | 0.48 | 0.48 |
|  | Purified water | Balance | Balance | Balance |
|  | Toluene-2,5-diamine | 0.40 | 0.40 | 0.40 |
|  | Para-aminophenol | 0.10 | 0.10 | 0.10 |
|  | Resorcin | 0.30 | 0.30 | 0.30 |
|  | Meta-aminophenol | 0.10 | 0.10 | 0.10 |
|  | 2,4-Diaminophenoxyethanol hydrochloride | 0.05 | 0.05 | 0.05 |
| (A) | Sodium polyoxyethylene laurylether sulfate | 0.72 | 3.60 | 3.60 |
| (A) | Sodium lauryl sulfate | — | — | — |
| (B) | Sodium cocoyl glutamate | 0.80 | 4.00 | 4.00 |
| (B) | Sodium polyoxyethylene(4.5)laurylether acetate | — | — | — |
|  | Polyoxyethylene alkyl(12-14) ether | 15.00 | 15.00 | 15.00 |
|  | Myristyl alcohol | 0.30 | 0.30 | 0.30 |
| (C) | Dimethyldiallylammonium chloride-acrylic acid (95:5) copolymer (*1) | 0.50 | 2.50 | 1.60 |
| (C) | Polychlorinated dimethylmethylene piperidinium (*2) | — | — | — |
|  | Dimethyldiallylammonium chloride-acrylic acid (65:35) copolymer (*3) | — | — | — |
|  | Ethanolamine | 5.00 | 5.00 | 5.00 |
|  | Ethanol | 5.00 | 5.00 | 5.00 |
|  | Total | 100 | 100 | 100 |
|  | Second agent |  |  |  |
|  | Cetyltrimethylammonium chloride | 0.57 | 0.57 | 0.57 |
|  | Stearyltrimethylammonium chloride | 0.19 | 0.19 | 1.19 |
| (A) | Sodium polyoxyethylene laurylether sulfate | — | — | — |
| (B) | Sodium cocoyl glutamate | — | — | — |
|  | Polyoxyethylene cetyl ether | 0.80 | 0.80 | 0.80 |
|  | Cetanol | 0.50 | 0.50 | 0.50 |
|  | Behenyl alcohol | 0.70 | 0.70 | 0.70 |
|  | Oxyquinoline sulfate | 0.04 | 0.04 | 0.04 |
|  | Hydroxyethanediphosphonic acid | 0.04 | 0.04 | 0.04 |
|  | Sodium hydroxide solution (48 mass %), phosphoric acid (75 mass %) | (*4) | (*4) | (*4) |
|  | Hydrogen peroxide (35 mass %) | 16.30 | 16.30 | 16.30 |

TABLE 3-continued

|  | Example | | |
|---|---|---|---|
| (Mass %) | 9 | 10 | 11 |
| Propylene glycol | 0.50 | 0.50 | 0.50 |
| Soft lanolin fatty acid | 0.05 | 0.05 | 0.05 |
| Purified water | Balance | Balance | Balance |
| Total | 100 | 100 | 100 |
| Mixed solution of first agent and second agent | | | |
| (A) | 0.24 | 1.2 | 1.2 |
| (B) | 0.27 | 1.33 | 1.33 |
| (C) | 0.17 | 0.83 | 0.53 |
| [(A) + (B)]/(C) | 3.04 | 3.04 | 4.75 |
| Evaluation on the foaming when applied to hair subjected to a treatment | 2 | 4 | 4 |
| Foam volume after applied to hair subjected to a treatment (mL) | 15 | 85 | 70 |

TABLE 4

|  |  | Comparative Example | |
|---|---|---|---|
| (Mass %) | | 1 | 2 |
| First agent | | | |
| Tetrasodium edetate dihydrate | | 0.10 | 0.10 |
| Ascorbic acid | | 0.40 | 0.40 |
| Sodium sulfite | | 0.48 | 0.48 |
| Purified water | | Balance | Balance |
| Toluene-2,5-diamine | | 0.40 | 0.40 |
| Para-aminophenol | | 0.10 | 0.10 |
| Resorcin | | 0.30 | 0.30 |
| Meta-aminophenol | | 0.10 | 0.10 |
| 2,4-Diaminophenoxyethanol hydrochloride | | 0.05 | 0.05 |
| (A) | Sodium polyoxyethylene laurylether sulfate | 2.16 | — |
| (A) | Sodium lauryl sulfate | — | — |
| (B) | Sodium cocoyl glutamate | 2.42 | 2.42 |
| (B) | Sodium polyoxyethylene(4.5)laurylether acetate | — | — |
| | Polyoxyethylene alkyl(12-14) ether | 15.00 | 15.00 |
| | Myristyl alcohol | 0.30 | 0.30 |
| (C) | Dimethyldiallylammonium chloride-acrylic acid (95:5) copolymer (*1) | — | 1.20 |
| (C) | Polychlorinated dimethylmethylene piperidinium (*2) | — | — |
| | Dimethyldiallylammonium chloride-acrylic acid (65:35) copolymer (*3) | 1.20 | — |
| | Ethanolamine | 5.00 | 5.00 |
| | Ethanol | 5.00 | 5.00 |
| | Total | 100 | 100 |
| Second agent | | | |
| | Cetyltrimethylammonium chloride | 0.57 | 0.57 |
| | Stearyltrimethylammonium chloride | 0.19 | 0.19 |
| (A) | Sodium polyoxyethylene laurylether sulfate | — | — |
| (B) | Sodium cocoyl glutamate | — | — |
| | Polyoxyethylene cetyl ether | 0.80 | 0.80 |
| | Cetanol | 0.50 | 0.50 |
| | Behenyl alcohol | 0.70 | 0.70 |
| | Oxyquinoline sulfate | 0.04 | 0.04 |
| | Hydroxyethanediphosphonic acid | 0.04 | 0.04 |
| | Sodium hydroxide solution (48 mass %), phosphoric acid (75 mass %) | (*4) | (*4) |
| | Hydrogen peroxide (35 mass %) | 16.30 | 16.30 |
| | Propylene glycol | 0.50 | 0.50 |
| | Soft lanolin fatty acid | 0.05 | 0.05 |
| | Purified water | Balance | Balance |
| | Total | 100 | 100 |
| Mixed solution of first agent and second agent | | | |
| (A) | | 0.72 | — |
| (B) | | 0.81 | 0.81 |
| (C) | | — | 0.4 |
| [(A) + (B)]/(C) | | — | 2.02 |
| Evaluation on the foaming when applied to hair subjected to a treatment | | 1 | 1 |
| Foam volume after applied to hair subjected to a treatment (mL) | | 5 | 3 |

The invention claimed is:

1. A cosmetic product, comprising:
a first agent comprising an alkali agent,
a second agent comprising hydrogen peroxide, and
a nonaerosol foamer container configured to discharge a mixed solution of the first agent and the second agent in the form of foam, the mixed solution comprising components (A) to (C):
(A) an anionic surfactant comprising a sulfuric acid group,
(B) an anionic surfactant comprising a carboxy group, and
(C) a polymer comprising a diallyl quaternary ammonium salt as a constitutional unit and having a charge density of from 5.5 meq/g to 8.0 meq/g,
wherein a content of component (B) in the mixed solution is from 0.4 mass % to 3 mass %,
wherein the component (B) is at least one selected from the group consisting of an N-acylamino acid salt and an ether acetate of formula (3):

$$R^2-Z-(CH_2CH_2O)_q-CH_2COOM^2 \qquad (3)$$

$R^2$ is a linear chain or branched chain alkyl group or alkenyl group having 7 to 19 carbon atoms,
Z is —O— or —CONH—,
$M^2$ is a hydrogen atom, an alkali metal atom, triethanolamine, or ammonium,
q is a number of 1 to 20, and
wherein the nonaerosol foamer container and the mixed solution are configured to discharge the foam with a volume of at least 20 mL per 7 g of mixed solution.

2. The cosmetic product according to claim 1, wherein a mass ratio of components (A) and (B), in total to component (C), [(A)+(B)]/(C), in the mixed solution is from 0.1 to 15.

3. The cosmetic product according to claim 1. wherein component (A) is a surfactant represented by formula (1):

$$R-O-(CH_2CH_2O)_n-[CH_2CH(CH_3)O]_m-SO_3M \qquad (1)$$

wherein

R represents a hydrocarbon group having 8 to 25 carbon atoms, n represents an average number of moles added of from 0 to 50, m represents an average number of moles added of from 0 to 50, and M represents an alkali metal atom or $NH_4$.

4. The cosmetic product according to claim 1, further comprising a cationic surfactant as a component (D).

5. The cosmetic product according to claim 4, wherein a content of component (D) in the mixed solution is from 0.05 mass % to 5 mass %.

6. The cosmetic product according to claim 1, further comprising a higher alcohol as a component (E).

7. The cosmetic product according to claim 6, wherein a content of component (E) in the mixed solution is from 0.05 mass % to 5 mass %.

8. The cosmetic product according to claim 1, wherein a content of component (A) in the mixed solution is from 0.01 mass % to 10 mass %.

9. The cosmetic product according to claim 1, wherein a content of component (C) in the mixed solution is from 0.01 mass % to 10 mass %.

10. The cosmetic product according to claim 1, wherein the total content of components (A) and (B) in the mixed solution is from above 0.4 mass % to 20 mass %.

11. The cosmetic product according to claim 1, wherein the nonaerosol container and the mixed solution are configured to discharge the foam with a volume of from 20 mL to 85 mL, per 7 g of mixed solution.

12. The cosmetic product according to claim 1, wherein a mass ratio of components (A) and (B), in total to component (C), [(A)+(B)]/(C), in the mixed solution is from 1.13 to 11.45.

13. A method for bleaching or dyeing hair with the cosmetic product of claim 1, the method comprising discharging the mixed solution of the first agent and the second agent from the nonaerosol foamer container in the form of foam, and applying the foam to hair.

14. A method according to claim 13, wherein said applying is carried out by hand.

15. The method of claim 13, wherein the foam has a volume of at least 20 mL per 7 g of mixed solution.

16. The method of claim 13, wherein the foam has a volume of from 20 mL to 85 mL, per 7 g of mixed solution.

* * * * *